US008080557B2

(12) United States Patent
Kennis et al.

(10) Patent No.: US 8,080,557 B2
(45) Date of Patent: Dec. 20, 2011

(54) QUINAZOLINEDIONE DERIVATIVES AS PARP INHIBITORS

(75) Inventors: Ludo Edmond Josephine Kennis, Lier (BE); Josephus Carolus Mertens, Oud-Turnhout (BE); Jacbous Alphonsus Josephus Van Dun, Kasterlee (BE); Maria Victorina Francisca Somers, Vosselaar (BE); Walter Boudewijn Leopold Wouters, Kapellen (BE)

(73) Assignee: Janssen Pharmaceutica, NV (BE)

( * ) Notice: Subject to any disclaimer, the term of this patent is extended or adjusted under 35 U.S.C. 154(b) by 1168 days.

(21) Appl. No.: 11/569,948

(22) PCT Filed: Jun. 28, 2005

(86) PCT No.: PCT/EP2005/053031
§ 371 (c)(1),
(2), (4) Date: Dec. 1, 2006

(87) PCT Pub. No.: WO2006/003148
PCT Pub. Date: Jan. 12, 2006

(65) Prior Publication Data
US 2008/0039480 A1  Feb. 14, 2008

(30) Foreign Application Priority Data
Jun. 30, 2004  (EP) .................... 04076885

(51) Int. Cl.
*A61K 31/517* (2006.01)
*A61K 31/519* (2006.01)
*C07D 239/72* (2006.01)

(52) U.S. Cl. .................. 514/266.22; 544/285
(58) Field of Classification Search .................. None
See application file for complete search history.

(56) References Cited

U.S. PATENT DOCUMENTS
3,274,194 A * 9/1966 Hayao .................. 544/285
3,919,425 A   11/1975 Vidrio et al.

FOREIGN PATENT DOCUMENTS
| EP | 0013612 B1 | 11/1983 |
| EP | 391462 A1 | 10/1990 |
| FR | 2436781 * | 4/1980 |
| WO | 1991/012006 A2 | 8/1991 |
| WO | WO 9322309 * | 11/1993 |
| WO | 1999/029687 A1 | 6/1999 |
| WO | 2002/048117 A1 | 6/2002 |

OTHER PUBLICATIONS

Takai et al. Chemical and Pharmaceutical Bulletin, 1986, 34(5), 1907-16.*
Herndon et al. Journal of Medicinal Chemistry, 1992, 35(26), 4903-10.*
Kornet et al. (Journal of Heterocyclic Chemistry, 1984, 21(5), 1533-35.*
Hazard et al. Therapie, 1965, 20(4), 1043-9.*
Calabrese et al. Journal of the National Cancer Institute, 2004, 96(1), 56-69.*
Tentori et al. Pharmacological Research, 2005, 52, 25-33.*
"Cancer definition", http://www.medterms.com/script/main/art.asp?articlekey=2580, accessed Nov. 27, 2007.*
"Prostate Cancer Prevention", http://www.cancer.gov/cancertopics/pdq/prevention/prostate/Patient, accessed Apr. 9, 2010.*
Takai, H., et al: "Synthesis of piperidine derivatives with a quinazoline ring system as potential antihypertensive agents", Chemical and Pharmaceutical Bulletin, Pharmaceutical Society of Japan, Tokyo, JP, vol. 34, No. 5, 1986, pp. 1907-1916, XP002333132, ISSN: 0009-2363, example 2a.
Hayao, S., et al:"New sedative and hypotensive 3-substituted 2,4(1H,3H)- quinazolidinediones" Journal of Medicinal Chemistry, vol. 8, 1965, pp. 807-811, XP002347459, the whole document.
Herndon, J.L. et al: "Ketanserin Analogues: Structure-Affinity Relationships for 5-HT2 and 5-HT1C Serotonin Receptor Binding" Journal of Medicinal Chemistry, American Chemical Society. Washington, US, vol. 35, 1992, pp. 4903-4910, XP000941731, ISSN: 0022-2623, table II; compounds 1,8-11,17.
Database WPI 'Online! Derwent Publications Ltd., London, GB; XP002347462, retrieved from WPI accession No. 1970-18449R, *see RN 27634-66-9: 3-(piperidin-1-yl-propyl)-1H-quinazoline-2,4-dione*, abstract & JP 45007058B (Sankyo) Jul. 6, 1967.
Costantino, G., et al: J. Med. Chem., vol. 44, No. 23, 2001, pp. 3786-3794, XP002347460, p. 3788.
International Search Report and Written Opinion, PCT/EP2005/053031, dated Oct. 25, 2005, 12 pages.

* cited by examiner

*Primary Examiner* — Noble Jarrell

(57) ABSTRACT

The present invention provides compounds of formula (I), their use as PARP inhibitors as well as pharmaceutical compositions comprising said compounds of formula (I)

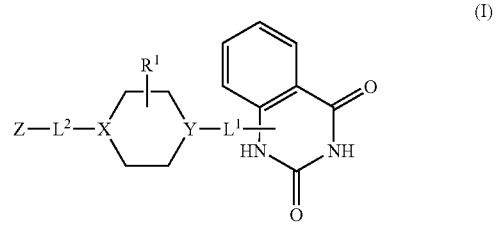

wherein $R^1$, $L^1$, $L^2$, X, Y and Z have defined meanings.

18 Claims, No Drawings

QUINAZOLINEDIONE DERIVATIVES AS PARP INHIBITORS

CROSS REFERENCE TO RELATED APPLICATIONS

This application is the national stage of Application No PCT/EP2005/053031, filed Jun. 28, 2005, which claims priority from EPO Patent Application No. 04076885.5 filed Jun. 30, 2004, the entire disclosures of which are hereby incorporated in their entirely.

FIELD OF THE INVENTION

The present invention relates to inhibitors of PARP and provides compounds and compositions containing the disclosed compounds. Moreover, the present invention provides methods of using the disclosed PARP inhibitors for instance as a medicine.

BACKGROUND OF THE INVENTION

The nuclear enzyme poly(ADP-ribose) polymerase-1 (PARP-1) is a member of the PARP enzyme family. This growing family of enzymes consist of PARPs such as, for example: PARP-1, PARP-2, PARP-3 and Vault-PARP; and Tankyrases (TANKs), such as, for example: TANK-1, TANK-2 and TANK-3. PARP is also referred to as poly(adenosine 5'-diphospho-ribose) polymerase or PARS (poly (ADP-ribose) synthetase).

Tankyrases (TANKs) were identified as components of the human telomeric complex. They have also been proposed to have a role in vesicle trafficking and may serve as scaffolds for proteins involved in various other cellular processes. Telomeres, which are essential for chromosome maintenance and stability, are maintained by telomerase, a specialized reverse transcriptase. TANKs are (ADP-ribose)transferases with some features of both signalling and cytoskeletal proteins. They contain the PARP domain, which catalyses poly-ADP-ribosylation of substrate proteins, the sterile alpha motif, which is shared with certain signalling molecules and the ANK domain, which contains 24 ankyrin repeats homologues to the cytoskeletal protein ankyrin. The ANK domain interacts with a telomeric protein, Telomere Repeat binding Factor-1 (TRF-1). These proteins were therefore named TRF1-interacting, ankyrin-related ADP-ribose polymerase (TANKs).

One of the more specific functions of TANK is the ADP-ribosylation of TRF-1. Human telomere function requires two telomere-specific DNA binding proteins, TRF-1 and TRF-2. TRF-2 protects chromosome ends, and TRF-1 regulates telomere length. ADP-ribosylation inhibits the ability of TRF-1 to bind to telomeric DNA. This poly-ADP-ribosylation of TRF-1 releases TRF-1 from the telomeres, opening up the telomeric complex and allow access to telomerase. Therefore, TANK functions as a positive regulator of telomere length, allowing elongation of the telomeres by telomerase.

PARP-1 is a major nuclear protein of 116 kDa consisting of three domains: the N-terminal DNA binding domain containing two zinc fingers, the automodification domain and the C-terminal catalytic domain. It is present in almost all eukaryotes. The enzyme synthesizes poly(ADP-ribose), a branched polymer that can consist of over 200 ADP-ribose units. The protein acceptors of poly(ADP-ribose) are directly or indirectly involved in maintaining DNA integrity. They include histones, topoisomerases, DNA and RNA polymerases, DNA ligases, and $Ca^{2+}$- and $Mg^{2+}$-dependent endonucleases.

PARP protein is expressed at a high level in many tissues, most notably in the immune system, heart, brain and germline cells. Under normal physiological conditions, there is minimal PARP activity. However, DNA damage causes an immediate activation of PARP by up to 500-fold.

Among the many functions attributed to PARP, and especially PARP-1, is its major role in facilitating DNA repair by ADP-ribosylation and therefore co-ordinating a number of DNA repair proteins. As a result of PARP activation, $NAD^+$ levels significantly decline. Extensive PARP activation leads to severe depletion of $NAD^+$ in cells suffering from massive DNA damage. The short half-life of poly(ADP-ribose) results in a rapid turnover rate. Once poly(ADP-ribose) is formed, it is quickly degraded by the constitutively active poly(ADP-ribose) glycohydrolase (PARG), together with phosphodiesterase and (ADP-ribose) protein lyase. PARP and PARG form a cycle that converts a large amount of $NAD^+$ to ADP-ribose. In less than an hour, over-stimulation of PARP can cause a drop of $NAD^+$ and ATP to less than 20% of the normal level. Such a scenario is especially detrimental during ischaemia when deprivation of oxygen has already drastically compromised cellular energy output. Subsequent free radical production during reperfusion is assumed to be a major cause of tissue damage. Part of the ATP drop, which is typical in many organs during ischaemia and reperfusion, could be linked to $NAD^+$ depletion due to poly(ADP-ribose) turnover. Thus, PARP or PARG inhibition is expected to preserve the cellular energy level thereby potentiating the survival of ischaemic tissues after insult.

Poly(ADP-ribose) synthesis is also involved in the induced expression of a number of genes essential for inflammatory response. PARP inhibitors suppress production of inducible nitric oxide synthase (iNOS) in macrophages, P-type selectin and intercellular adhesion molecule-1 (ICAM-1) in endothelial cells. Such activity underlies the strong anti-inflammation effects exhibited by PARP inhibitors. PARP inhibition is able to reduce necrosis by preventing translocation and infiltration of neutrophils to the injured tissues.

PARP is activated by damaged DNA fragments and, once activated, catalyzes the attachment of up to 100 ADP-ribose units to a variety of nuclear proteins, including histones and PARP itself. During major cellular stresses the extensive activation of PARP can rapidly lead to cell damage or death through depletion of energy stores. As four molecules of ATP are consumed for every molecule of $NAD^+$ regenerated, $NAD^+$ is depleted by massive PARP activation, in the efforts to re-synthesize $NAD^+$, ATP may also become depleted.

It has been reported that PARP activation plays a key role in both NMDA- and NO-induced neurotoxicity. This has been demonstrated in cortical cultures and in hippocampal slices wherein prevention of toxicity is directly correlated to PARP inhibition potency. The potential role of PARP inhibitors in treating neurodegenerative diseases and head trauma has thus been recognized even if the exact mechanism of action has not yet been elucidated.

Similarly, it has been demonstrated that single injections of PARP inhibitors have reduced the infarct size caused by ischemia and reperfusion of the heart or skeletal muscle in rabbits. In these studies, a single injection of 3-amino-benzamide (10 mg/kg), either one minute before occlusion or one minute before reperfusion, caused similar reductions in infarct size in the heart (32-42%) while 1,5-dihydroxyisoquinoline (1 mg/kg) another PARP inhibitor, reduced infarct size by a comparable degree (M3-48%) These results make it reasonable to assume that PARP inhibitors could salvage previously ischaemic heart or reperfusion injury of skeletal muscle tissue.

PARP activation can also be used as a measure of damage following neurotoxic insults resulting from exposure to any of the following inducers like glutamate (via NMDA receptor stimulation), reactive oxygen intermediates, amyloid β-protein, N-methyl-4-phenyl-1,2,3,6-tetrahydropyridine (MPTP) or its active metabolite N-methyl-4 phenylpyridine (MPP+), which participate in pathological conditions such as stroke, Alzheimer's disease and Parkinson's disease. Other studies have continued to explore the role of PARP activation in cerebellar granule cells in vitro and in MPIP neurotoxicity. Excessive neural exposure to glutamate, which serves as the predominate central nervous system neurotransmitter and acts upon the N-methyl D-aspartate (NMDA) receptors and other subtype receptors, most often occurs as a result of stroke or other neurodegenerative processes. Oxygen deprived neurons release glutamate in great quantities during ischaemic brain insult such as during a stroke or heart attack.

This excess release of glutamate in turn causes over-stimulation (excitotoxicity) of N-methyl-D-aspartate (NMDA), AMPA, Kainate and MGR receptors, which open ion channels and permit uncontrolled ion flow (e.g., $Ca^{2+}$ and $Na^+$ into the cells and $K^+$ out of the cells) leading to overstimulation of the neurons. The over-stimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoxia, hypoglycemia, ischemia, trauma, and nervous insult. Glutamate exposure and stimulation has also been implicated as a basis for compulsive disorders, particularly drug dependence. Evidence includes findings in many animal species, as well as in cerebral cortical cultures treated with glutamate or NMDA, that glutamate receptor antagonists (i.e., compounds which block glutamate from binding to or activating its receptor) block neural damage following vascular stroke. Attempts to prevent excitotoxicity by blocking NMDA, AMPA, Kainate and MGR receptors have proven difficult because each receptor has multiple sites to which glutamate may bind and hence finding an effective mix of antagonists or universal antagonist to prevent binding of glutamate to all of the receptor and allow testing of this theory, has been difficult. Moreover, many of the compositions that are effective in blocking the receptors are also toxic to animals. As such, there is presently no known effective treatment for glutamate abnormalities. The stimulation of NMDA receptors by glutamate, for example, activates the enzyme neuronal nitric oxide synthase (nNOS), leading to the formation of nitric oxide (NO), which also mediates neurotoxicity. NMDA neurotoxicity may be prevented by treatment with nitric oxide synthase (NOS) inhibitors or through targeted genetic disruption of nNOS in vitro.

Another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs.

Evidence also exists that PARP inhibitors are useful for treating inflammatory bowel disorders, such as colitis. Specifically, colitis was induced in rats by intraluminal administration of the hapten trinitrobenzene sulfonic acid in 50% ethanol. Treated rats received 3-aminobenzamide, a specific inhibitor of PARP activity. Inhibition of PARP activity reduced the inflammatory response and restored the morphology and the energetic status of the distal colon.

Further evidence suggests that PARP inhibitors are useful for treating arthritis. Further, PARP inhibitors appear to be useful for treating diabetes. PARP inhibitors have been shown to be useful for treating endotoxic shock or septic shock.

PARP inhibitors have also been used to extend the lifespan and proliferative capacity of cells including treatment of diseases such as skin aging, Alzheimer's disease, atherosclerosis, osteoarthritis, osteoporosis, muscular dystrophy, degenerative diseases of skeletal muscle involving replicative senescence, age-related muscular degeneration, immune senescence, AIDS, and other immune senescence disease; and to alter gene expression of senescent cells.

It is also known that PARP inhibitors, such as 3-amino benzamide, affect overall DNA repair in response, for example, to hydrogen peroxide or ionizing radiation.

The pivotal role of PARP in the repair of DNA strand breaks is well established, especially when caused directly by ionizing radiation or, indirectly after enzymatic repair of DNA lesions induced by methylating agents, topoisomerases I inhibitors and other chemotherapeutic agents as cisplatin and bleomycin. A variety of studies using, "knockout" mice, trans-dominant inhibition models (over-expression of the DNA-binding domain), antisense and small molecular weight inhibitors have demonstrated the role of PARP in repair and cell survival after induction of DNA damage. The inhibition of PARP enzymatic activity should lead to an enhanced sensitivity of the tumor cells towards DNA damaging treatments.

PARP inhibitors have been reported to be effective in radiosensitizing (hypoxic) tumor cells and effective in preventing tumor cells from recovering from potentially lethal and sub-lethal damage of DNA after radiation therapy, presumably by their ability to prevent DNA strand break rejoining and by affecting several DNA damage signaling pathways.

PARP inhibitors have been used to treat cancer. In addition, U.S. Pat. No. 5,177,075 discusses several isoquinolines used for enhancing the lethal effects of ionizing radiation or chemotherapeutic agents on tumor cells. Weltin et al., "Effect of 6(5-Phenanthridinone), an Inhibitor of Poly(ADP-ribose) Polymerase, on Cultured Tumor Cells", Oncol. Res., 6:9, 399-403 (1994), discusses the inhibition of PARP activity, reduced proliferation of tumor cells, and a marked synergistic effect when tumor cells are co-treated with an alkylating drug.

Reviews of the state of the art has been published by Li and Zhang in IDrugs 2001, 4(7): 804-812, by Ame et al in Bioassays 2004, 26: 882-883 and by Nguewa et al., in Progress in Biophysic & Molecular Biology 2005, 88: 143-172.

There continues to be a need for effective and potent PARP inhibitors, and more particularly PARP-1 inhibitors which produce minimal side effects. The present invention provides compounds, compositions for, and methods of, inhibiting PARP activity for treating cancer and/or preventing cellular, tissue and/or organ damage resulting from cell damage or death due to, for example, necrosis or apoptosis. The compounds and compositions of the present invention are especially useful in enhancing the effectiveness of chemotherapy and radiotherapy where a primary effect of the treatment is that of causing DNA damage in the targeted cells.

BACKGROUND PRIOR ART

EP 1036073, published on Jun. 17, 1999, discloses substituted quinazolinedione derivatives. The described compounds have fundic relaxation properties. More in particular the compound 1-[1-[(2S)-2-[(2R)-3,4-dihydro-2H-1-benzopyran-2-yl]-2-hydroxyethyl]-4-piperidinyl]-2,4 (1H,3H)-quinazolinedione (compound No. 9 of the present application) is disclosed.

compound 9

EP 13612, published on Nov. 11, 1983, discloses substituted piperidinylalkylquinazoline derivatives. The described compounds are serotonin-antagonists. More in particular the compounds 1-[2-[4-(4-fluorobenzoyl)-1-piperidinyl]ethyl]-2,4-(1H, 3H)-quinazolinedione (compound No. 10 of the present application) 1-[3-[4-(4-fluorobenzoyl)-1-piperidinyl]propyl]-2,4-(1H, 3H)-quinazolinedione (compound No. 11 of the present application), 3-[2-[4-(4-chlorobenzoyl)-1-piperidinyl]ethyl]-2,4-(1H, 3H)-quinazolinedione (compound No. 12 of the present application) 3-[2-[4-[(4-fluorophenyl)hydroxymethyl]-1-piperidinyl]ethyl]-2,4-(1H, 3H) -quinazolinedione (compound No. 13 of the present application) are disclosed.

compound 10 compound 11 compound 12 compound 13

DESCRIPTION OF THE INVENTION

This invention concerns compounds of formula (I)

(I)

$$Z-L^2-X\quad Y-L^1$$

the N-oxide forms, the pharmaceutically acceptable addition salts and the stereo-chemically isomeric forms thereof, wherein each X is independently $$\text{\textbackslash}N-, \quad \text{or} \quad \text{\textbackslash}CH-;$$

and when X is $$\text{\textbackslash}CH-$$

then Y is $$\text{\textbackslash}N-;$$

each Y is independently $$\text{\textbackslash}N-, \quad \text{or} \quad \text{\textbackslash}CH-;$$

except when X is $$\text{\textbackslash}CH-$$

then Y is $$\text{\textbackslash}N-;$$

L¹ is a direct bond or a bivalent radical selected from —C₁₋₆alkanediyl-;
L² is a direct bond or a bivalent radical selected from carbonyl, —C₁₋₆alkanediyl-, -(hydroxy)C₁₋₆alkanediyl-, —C(O)—C₁₋₆alkanediyl- or —C₁₋₆alkanediyl-C(O)—;
R¹ is hydrogen or hydroxy;
Z is hydrogen or a radical selected from

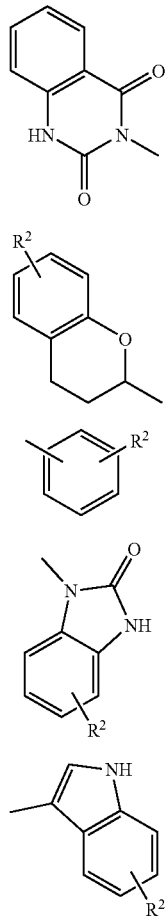

wherein each R² is independently selected from hydrogen, halo or C₁₋₆alkyl,
with the proviso that 1-[1-[(2S)-2-[(2R)-3,4-dihydro-2H-1-benzopyran-2-yl]-2-hydroxyethyl]-4-piperidinyl]-2,4 (1H, 3H)-quinazolinedione, 1-[2-[4-(4-fluorobenzoyl)-1-piperidinyl]ethyl]-2,4-(1H, 3H)-quinazolinedione, 1-[3-[4-(4-fluorobenzoyl)-1-piperidinyl]propyl]-2,4-(1H, 3H)-quinazolinedione, 3-[2-[4-(4-chlorobenzoyl)-1-piperidinyl]ethyl]-2,4-(1H, 3H)-quinazolinedione and 3-[2-[4-[(4-fluorophenyl)hydroxymethyl]-1-piperidinyl]ethyl]-2,4-(1H, 3H)-quinazolinedione are not included.

Whenever Z is the heterocyclic ring system containing a CH₂—, —CH═, or —NH— moiety, the substituent R² and/or the rest of the molecule, can be attached to the carbon and/or nitrogen atom in which case one or both hydrogen atoms are replaced.

In the compounds of formula (I), the quinazolinedione moiety can be attached to the rest of the molecule on the —NH-moieties in the 1- or the 3-position in which case a hydrogen atom is replaced.

The compounds of formula (I) may also exist in their tautomeric forms. Such forms although not explicitly indicated in the above formula are intended to be included within the scope of the present invention.

A number of terms used in the foregoing definitions and hereinafter are explained hereunder. These terms are sometimes used as such or in composite terms.

As used in the foregoing definitions and hereinafter, halo is generic to fluoro, chloro, bromo and iodo; C₁₋₆alkyl defines straight and branched chain saturated hydrocarbon radicals having from 1 to 6 carbon atoms such as, e.g. methyl, ethyl, propyl, butyl, pentyl, hexyl, 1-methylethyl, 2-methylpropyl, 2-methyl-butyl, 2-methylpentyl and the like; C₁₋₆alkanediyl defines bivalent straight and branched chained saturated hydrocarbon radicals having from 1 to 6 carbon atoms such as, for example, methylene, 1,2-ethanediyl, 1,3-propanediyl 1,4-butanediyl, 1,5-pentanediyl, 1,6-hexanediyl and the branched isomers thereof such as, 2-methylpentanediyl, 3-methylpentanediyl, 2,2-dimethylbutanediyl, 2,3-dimethylbutanediyl and the like.

The term "pharmaceutically acceptable salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine- or piperazine nitrogens are N-oxidized.

Whenever used hereinafter, the term "compounds of formula (I)" is meant to include also the N-oxide forms, the pharmaceutically acceptable acid or base addition salts and all stereoisomeric forms.

The compounds described in EP 1036073 have fundic relaxation properties. 1-[1-[(2S)-2-[(2R)-3,4-dihydro-2H-1-benzopyran-2-yl]-2-hydroxyethyl]-4-piperidnyl]-2,4 (1H, 3H)-quinazolinedione (compound No. 9 of the present application) has been disclosed in EP 1036073. The compounds in EP 13612, are serotonin-antagonists. 1-[2-[4-(4-fluorobenzoyl)-1-piperidinyl]ethyl]-2,4-(1H, 3H)-quinazolinedione (compound No. 10 of the present application), 1-[3-[4-(4-fluorobenzoyl)-1-piperidinyl]propyl]-2,4-(1H, 3H)-quinazolinedione (compound No. 11 of the present application), 3-[2-[4-(4-chlorobenzoyl)-1-piperidinyl]ethyl]-2,4-(1H, 3H)-quinazolinedione (compound No. 12 of the present application) 3-[2-[4-[(4-fluorophenyl)hydroxymethyl]-1-piperidinyl]ethyl]-2,4-(1H, 3H)quinazolinedione (compound No. 13 of the present application) are disclosed.

Unexpectedly, it has been found that the compounds of the present invention show PARP inhibitory activity.

A first group of interesting compounds consists of those compounds of formula (I) wherein one or more of the following restrictions apply:

a) each X is independently

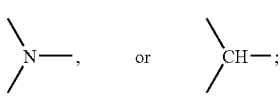

b) each Y is independently

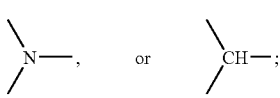

c) $L^1$ is a direct bond or a bivalent radical selected from —$C_{1-6}$alkanediyl-;

d) $L^2$ is a direct bond or a bivalent radical selected from carbonyl, —$C_{1-6}$alkanediyl-, -(hydroxy)$C_{1-6}$alkanediyl-, or —C(O)—$C_{1-6}$alkanediyl-;

e) $R^1$ is hydrogen or hydroxy;

f) Z is hydrogen or a radical selected from (a-1), (a-2), (a-3), (a-4) or (a-5);

g) each $R^2$ is independently selected from hydrogen, halo or $C_{1-6}$alkyl.

A second group of interesting compounds consists of those compounds of formula (I) wherein one or more of the following restrictions apply:

a) $L^2$ is a direct bond or a bivalent radical selected from —$C_{1-6}$alkanediyl - or —C(O)—$C_{1-6}$alkanediyl-;

b) Z is hydrogen or a radical selected from (a-1), (a-4) or (a-5).

A third group of interesting compounds consists of those compounds of formula (I) wherein one or more of the following restrictions apply:

a) each X is

b) each Y is

c) $L^1$ is a direct bond;
d) $L^2$ is a direct bond;
e) $R^1$ is hydrogen;
f) Z is hydrogen;

A group of preferred compounds consists of those compounds of formula (I) wherein each X is independently

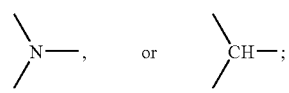

each Y is independently

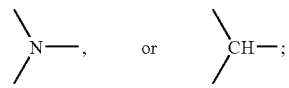

$L^1$ is a direct bond or a bivalent radical selected from —$C_{1-6}$alkanediyl-; $L^2$ is a direct bond or a bivalent radical selected from carbonyl or —$C_{1-6}$alkanediyl-; Rt is hydrogen or hydroxy;

Z is hydrogen or a radical selected from (a-1), (a-2), (a-3), (a-4) or (a-5); and each $R^2$ is independently selected from hydrogen, halo or $C_{1-6}$alkyl.

A group of more preferred compounds consists of those compounds of formula (I) wherein each X is

each Y is

$L^1$ is a direct bond; $L^2$ is a direct bond; $R^1$ is hydrogen; and Z is hydrogen.

The most preferred compound is compound No 1.

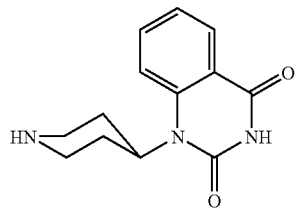

compound 1

The compounds of formula (I) can be prepared according to the general methods described in EP1036073 and EP13612. The starting materials and some of the intermediates are known compounds and are commercially available or may be tab prepared according to conventional reaction procedures generally known in the art. Some preparation methods will be described hereinafter in more detail. Other methods for obtaining final compounds of formula (I) are described in the examples.

The compounds of formula (I), wherein X is

herein referred to as compounds of formula (I-a), can be prepared by reacting an intermediate of formula (II), with an intermediate of formula (III), wherein W is an appropriate leaving group such as, for example, halo, e.g. fluoro, chloro, bromo or iodo, or a sulfonyloxy radical such as methylsulfonyloxy, 4-methylphenylsulfonyloxy and the like. The reaction can be performed in a reaction-inert solvent such as, for example, an alcohol, e.g. methanol, ethanol, 2-methoxy-ethanol, propanol, butanol and the like; an ether, e.g. 4,4-dioxane, 1,1'-oxybispropane and the like; or a ketone, e.g. 4-methyl-2-pentanone, N,N-dimethylformamide, nitrobenzene and the like. The addition of an appropriate base such as, for example, an alkali or earth alkaline metal carbonate or hydrogen carbonate, e.g. triethylamine or sodium carbonate, may be utilized to pick up the acid which is liberated during the course of the reaction. A small amount of an appropriate metal iodide, e.g., sodium or potassium iodide may be added to promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

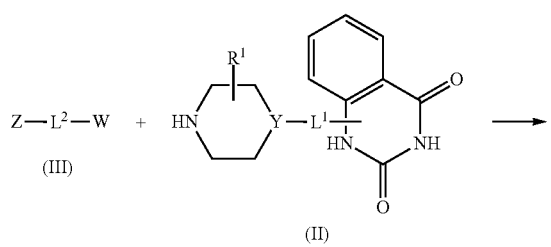

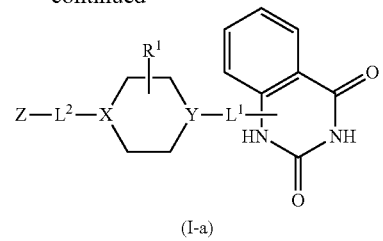

(I-a)

In an analogues way, the compounds of formula (I), wherein Y is

herein referred to as compounds of formula (I-b), can be prepared by reacting an intermediate of formula (IV), with an intermediate of formula (V) wherein W is as described above.

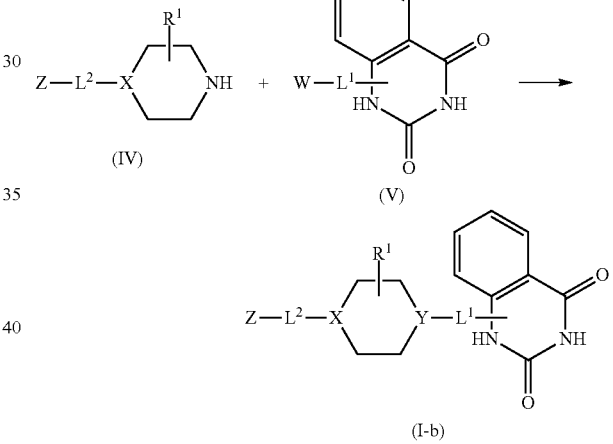

The compounds of formula (I) may also be converted into each other via art-known reactions or functional group transformations. Some of such transformations are already described hereinabove. Other examples are hydrolysis of carboxylic esters to the corresponding carboxylic acid or alcohol; hydrolysis of amides to the corresponding carboxylic acids or amines; hydrolysis of nitrites to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

The present invention also relates to a compound of formula (I) as defined above for use as a medicine.

The compounds of the present invention have PARP inhibiting properties as can be seen from the experimental part hereinunder.

The term "PARP" is used herein to mean a protein having poly-ADP-ribosylation activity. Within the meaning of this term, PARP encompass all proteins encoded by a parp gene, mutants thereof, and alternative slice proteins thereof. Additionally, as used herein, the term "PARP" includes PARP analogues, homologues and analogues of other animals.

The term "PARP", includes but is not limited to PARP-1. Within the meaning of this term PARP-2, PARP-3, Vault-PARP (PARP-4), PARP-7 (TiPARP), PARP-8, PARP-9 (Bal), PARP-10, PARP-11, PARP-12, PARP-13, PARP-14, PARP-15, PARP-16, TANK-1, TANK-2, and TANK-3 may be encompassed.

Compounds that inhibit both PARP-1 and tankyrase 2 can have advantageous properties in that they have enhanced growth inhibiting activities in cancer cells.

The present invention also contemplates the use of compounds in the preparation of a medicament for the treatment of any of the diseases and disorders in an animal described herein, wherein said compounds are compounds of formula (I)

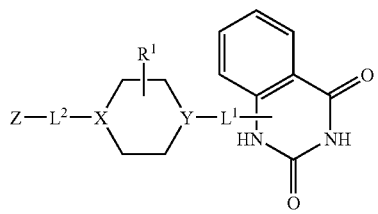
(I)

the N-oxide forms, the pharmaceutically acceptable addition salts and the stereo-chemically isomeric forms thereof, wherein
each X is independently

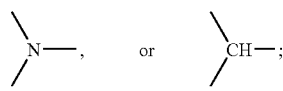

and when X is

then Y is

each Y is independently

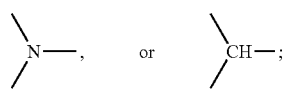

except when X is

then Y is

$L^1$ is a direct bond or a bivalent radical selected from $—C_{1-6}$ alkanediyl-;
$L^2$ is a direct bond or a bivalent radical selected from carbonyl, $—C_{1-6}$alkanediyl-, (hydroxy)$C_{1-6}$alkanediyl-, $—C(O)—C_{1-6}$alkanediyl- or $—C_{1-6}$alkanediyl -C(O)—;
$R^1$ is hydrogen or hydroxy;
and Z is hydrogen or a radical selected from

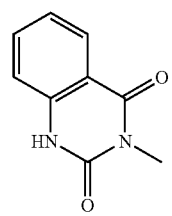
(a-1)

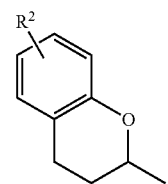
(a-2)

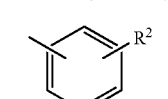
(a-3)

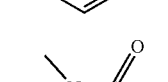
(a-4)

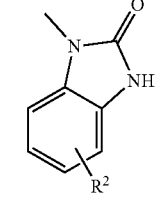
(a-5)

wherein each $R^2$ is independently selected from hydrogen, halo or $C_{1-6}$alkyl.

In view of their PARP binding properties the compounds of the present invention may be used as reference compounds or tracer compounds in which case one of the atoms of the molecule may be replaced with, for instance, a radioactive isotope.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of the present invention can treat or prevent tissue damage resulting from cell damage or death due to necrosis or apoptosis; can ameliorate neural or cardiovascular tissue damage, including that following focal ischemia, myocardial infarction, and reperfusion injury; can treat various diseases and conditions caused or exacerbated by PARP activity; can extend or increase the lifespan or proliferative capacity of cells; can alter the gene expression of senescent cells; can radiosensitize and/or chemosensitize cells. Generally, inhibition of PARP activity spares the cells from energy loss, preventing, in the case of neural cells, irreversible depolarization of the neurons, and thus, provides neuroprotection.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related muscular degeneration, AIDS and other immune senescence diseases, inflammation, gout, arthritis, atherosclerosis, cachexia, cancer, degenerative diseases of skeletal muscle involving replicative senescence, diabetes, head trauma, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging, to extend the lifespan and proliferative capacity of cells; to alter gene expression of senescent cells; chemosensitize and/or radiosensitize (hypoxic) tumor cells. The present invention also relates to treating diseases and conditions in an animal which comprises administering to said animal a therapeutically effective amount of the above-identified compounds.

In particular, the present invention relates to a method of treating, preventing or inhibiting a neurological disorder in an animal, which comprises administering to said animal a therapeutically effective amount of the above-identified compounds. The neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

The present invention also contemplates the use of compounds of formula (I) for inhibiting PARP activity, for treating, preventing or inhibiting tissue damage resulting from cell damage or death due to necrosis or apoptosis, for treating, preventing or inhibiting a neurological disorder in an animal.

The term "preventing neurodegeneration" includes the ability to prevent neurodegeneration in patients newly diagnosed as having a neurodegenerative disease, or at risk of developing a new degenerative disease and for preventing further neurodegeneration in patients who are already suffering from or have symptoms of a neurodegenerative disease.

The term "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation. Diseases which are treatable with ionizing radiation include neoplastic diseases, benign and malignant tumors, and cancerous cells. Ionizing radiation treatment of other diseases not listed herein are also contemplated by the present invention.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics. Diseases which are treatable with chemotherapy include neoplastic diseases, benign and malignant tumors and cancerous cells. Chemotherapy treatment of other diseases not listed herein are also contemplated by the present invention.

The compounds, compositions and methods of the present invention are particularly useful for treating or preventing tissue damage resulting from cell death or damage due to necrosis or apoptosis.

The compounds of the present invention can be "anti-cancer agents", which term also encompasses "anti-tumor cell growth agents" and "anti-neoplastic agents". For example, the methods of the invention are useful for treating cancers and chemosensitizing and/or radiosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft tissue sarcoma, squamous cell carcinomas, stomach cancer, testicular cancer, thyroid cancer, trophoblastic neoplasms, uterine cancer, vaginal cancer, cancer of the vulva and Wilm's tumor.

Hence the compounds of the present invention can be used as "radiosensitizer" and/or "chemosensitizer".

Radiosensitizers are known to increase the sensitivity of cancerous cells to the toxic effects of ionizing radiation. Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizingagent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'deoxythymidine, oxygen, carbogen, red cell transfusions, perfluorocarbons (e.g., Fluosol 10 DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumor or other therapeutically effective compounds for treating cancer or other disease. Examples of additional therapeutica agents that may be used in conjunction with chemosensitizers include, but are not limited to: methylating agents, toposisomerase I inhibitors and other chemothearpeutic agents such as cisplatin and bleomycin.

The compounds of formula (I) can also be used to detect or identify the PARP, and more in particular the PARP-1 receptor. For that purpose the compounds of formula (I) can be labeled. Said label can be selected from the group consisting of a radioisotope, spin label, antigen label, enzyme label fluorescent group or a chemiluminiscent group.

Those skilled in the art could easily determine the effective amount from the test results presented hereinafter. In general it is contemplated that an effective amount would be from 0.001 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.05 to 500 mg, and in particular 0.1 mg to 200 mg of active ingredient per unit dosage form.

The following examples illustrate the present invention.

EXPERIMENTAL PART

Hereinafter, "DCM" is defined as dichloromethane, "DIPE" is defined as diisopropyl ether, "DMF" is defined as N,N-dimethylformamide, "EtOH" is defined as ethanol, "MeOH" is defined as methanol, "MEK" is defined as methyl ethyl keton and "TEA" is defined as triethylamine, "THF" is defined as tetrahydrofuran.

A. Preparation of the Intermediate Compounds

EXAMPLE A1

Preparation of Intermediate 1

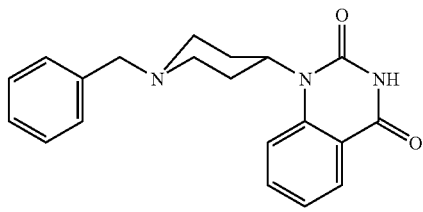

A mixture of 2-[[1-(phenylmethyl)-4-piperidinyl]amino]-benzamide (0.03 mol) and 1,1'-carbonylbis-1H-imidazole (0.033 mol) in dimethylacetamide (25 ml) was stirred and refluxed for 5 hours, then extra 1,1'-carbonylbis-1H-imidazole (0.003 mol) was added and the reaction mixture was stirred and refluxed overnight. The mixture was poured out into water (300 ml), then the resulting precipitate was filtered off, washed with water and with DIPE and dried (to give 9.1 g-91%). A part was then crystallised from DMF and water, finally the desired product was collected, yielding 0.8 g of intermediate 1, melting point 233.5° C.

B. Preparation of the Final Compounds

EXAMPLE B1

Preparation of Compound 1

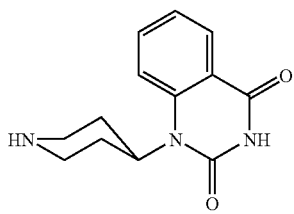

A mixture of intermediate 1 (0.15 mol) in THF (250 ml) and MeOH (250 ml) was hydrogenated in a Parr-apparatus with Pd/C 10% (5 g) as a catalyst. After uptake of $H_2$ (1 equiv.), the catalyst was filtered off, to give a filtrate (1) and a remaining precipitate on the filter. This precipitate was stirred in boiling hydroxyacetone and the mixture was filtered off hot. This filtrate was combined with filtrate (I) and the mixture was evaporated. The residue was stirred in water, then $NH_4OH$ was added and the mixture was stirred for 1 hour with trichloromethane. The precipitate was filtered off and dried, yielding 31 g (84%) of compound 1, melting point 253.7° C.

EXAMPLE B2

Preparation of Compound 2

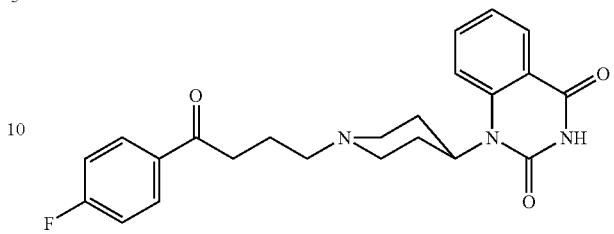

Compound 1 (0.038 mol) in 2-methoxy-ethanol (150 ml) was stirred and warmed until complete dissolution, then a solution of 1-(4-fluorophenyl)-4-iodo-1-butanone (0.019 mol) in 2-methoxy-ethanol (10 ml) was added dropwise under warming (precipitation occurred). The reaction mixture was stirred and refluxed for 1.5 hours. The precipitate was filtered off and the filtrate was evaporated. The residue was purified over silica gel on a glass filter (eluent: $CHCl_3$/MeOH 90/10). The product fractions were collected and the solvent was evaporated. The residue was crystallised from 2-propanol and then the resulting precipitate was collected and dried, yielding 2.3 g (29%) of compound 2, melting point 195° C.

EXAMPLE B3

Preparation of Compound 3

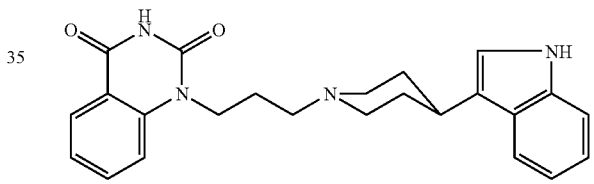

A mixture of 1-(3-chloropropyl)-2,4(1H,3H)-quinazolinedione (0.015 mol), 3-(4 piperidinyl)-1H-indole (0.015 mol) and sodium carbonate (0.030 mol) in 4-methyl-2-pentanone (150 ml) was stirred and refluxed for 24 hours, then the reaction mixture was cooled and water was added. The separated organic layer was dried and the solvent was evaporated. The residue was purified by column chromatography over silica gel (eluent: $CHCl_3/CH_3OH$ 95/5). The product fractions were collected and the solvent was evaporated. The residue was crystallised from EtOH and the resulting precipitate was collected, yielding 2 g (33%) of compound 3, melting point 216.8° C. Table F-1 lists the compound that were prepard according to one of the above Examples.

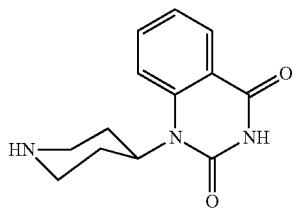

Co. No. 1; Ex. [B1]; mp. 253.7° C.

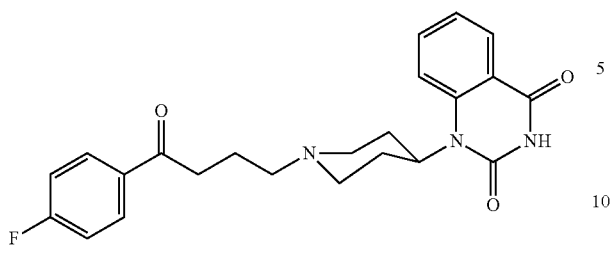
Co. No. 2; Ex. [B2]; mp. 195° C.
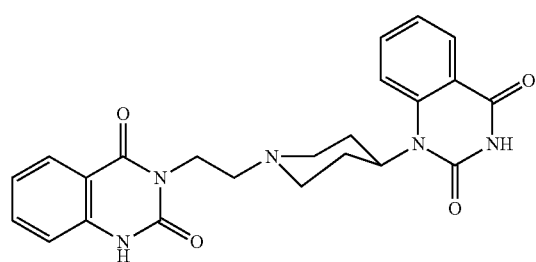
Co. No. 4; Ex. [B1]; mp. 266.6° C.
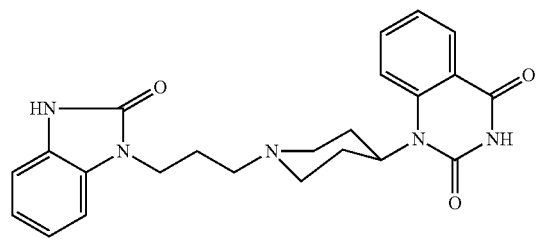
Co. No. 5; Ex. [B1]; mp. 222.2° C.
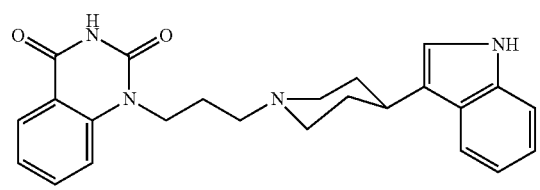
Co. No. 3; Ex. [B3]; mp. 216.8° C.
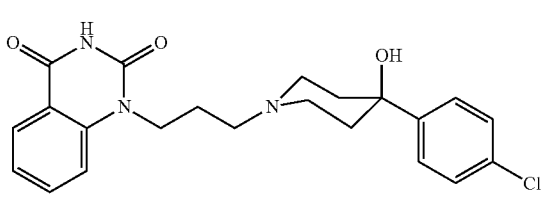
•HCl (1:1)•H$_2$O (1:1) Co. No. 6; Ex. [B3]; mp. 212.6° C.
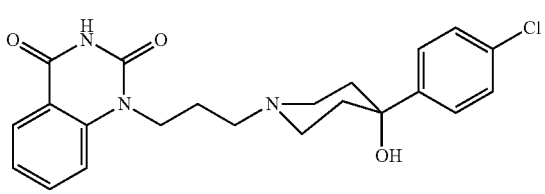
Co. No. 7; Ex. [B3]; mp. 186.3° C.
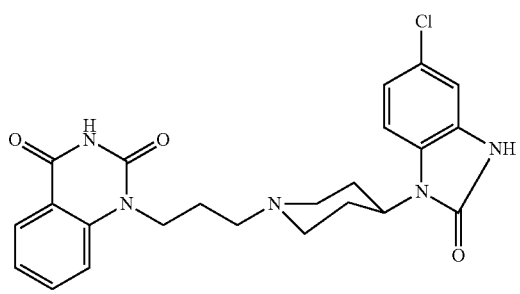
•HCl (1:1)•H$_2$O (2:1)•C$_2$H$_6$O (1:1); Co. No. 8; Ex. [B3]; mp >260° C.
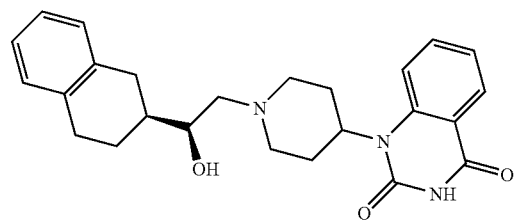
Co. No. 9; WO99/29687
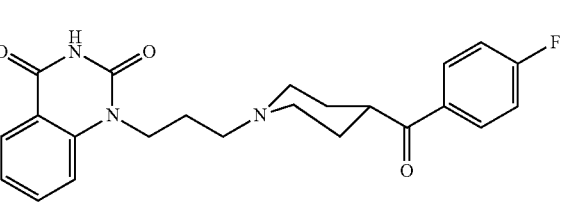
Co. No. 10; mp. 219.7° C., EP13612
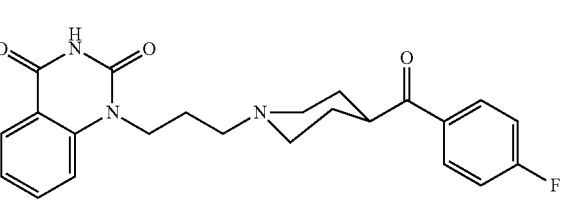
Co. No. 11; mp 192.9° C., EP13612
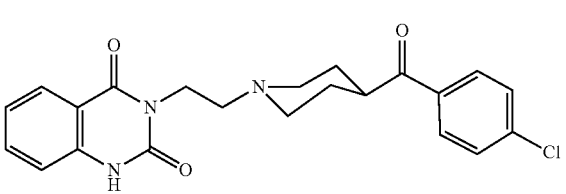
Co. No. 12; EP13612
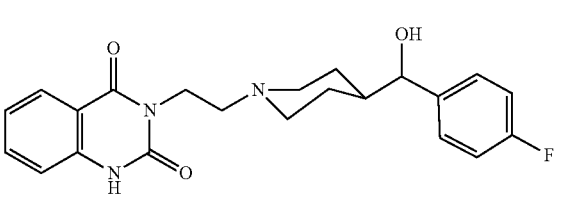
Co. No. 13; EP13612

PHARMACOLOGICAL EXAMPLE

In vitro Scintillation Proximity Assay (SPA) for PARP-1 Inhibitory Activity

Compounds of the present invention were tested in an in vitro assay based on SPA technology (proprietary to Amersham Pharmacia Biotech).

In principle, the assay relies upon the well established SPA technology for the detection of poly(ADP-ribosyl)ation of biotinylated target proteins, i.e histones. This ribosylation is induced using nicked DNA activated PARP-1 enzyme and [$^3$H]-nicotinamide adenine dinucleotide ([$^3$H]-NAD$^+$) as ADP-ribosyl donor.

As inducer of PARP-1 enzyme activity, nicked DNA was prepared. For this, 25 mg of DNA (supplier: Sigma) was dissolved in 25 ml DNAse buffer (10 mM Tris-HCl, pH 7.4; 0.5 mg/ml Bovine Serum Albumine (BSA); 5 mM MgCl$_2$.6H$_2$O and 1 mM KCl) to which 50 µl DNAse solution (1 mg/ml in 0.15 M NaCl) was added. After an incubation of 90 min. at 37° C., the reaction was terminated by adding 1.45 g NaCl, followed by a further incubation at 58° C. for 15 min. The reaction mixture was cooled on ice and dialysed at 4° C. for respectively 1.5 and 2 hours against 1.5 l of 0.2 M KCl, and twice against 1.5 l of 0.01 M KCl for 1.5 and 2 h respectively. The mixture was aliquoted and stored at −20° C. Histones (1 mg/ml, type II-A, supplier: Sigma) were biotinylated using the biotinylation kit of Amersham and stored aliquoted at −20° C. A stock solution of 100 mg/ml SPA poly(vinyl toluene) (PVT) beads (supplier: Amersham) was made in PBS. A stock solution of [$^3$H]-NAD$^+$ was made by adding 120 µl of [$^3$H]-NAD$^+$ (0.1 mCi/ml, supplier: NEN) to 6 ml incubation buffer (50 mM Tris/HCl, pH 8; 0.2 mM DTT; 4 mM MgCl$_2$). A solution of 4 mM NAD$^+$ (supplier: Roche) was made in incubation buffer (from a 100 mM stock solution in water stored at −20° C.). The PARP-1 enzyme was produced using art known techniques, i.e. cloning and expression of the protein starting from human liver cDNA. Information concerning the used protein sequence of the PARP-1 enzyme including literature references can be found in the Swiss-Prot database under primary accession number P09874. Biotinylated histones and PVT-SPA beads were mixed and pre-incubated for 30 min. at room temperature. PARP-1 enzyme (concentration was lot dependent) was mixed with the nicked DNA and the mixture was pre-incubated for 30 min. at 4° C. Equal parts of this histones/PVT-SPA beads solution and PARP-1 enzyme/DNA solution were mixed and 75 µl of this mixture together with 1 µl of compound in DMSO and 25 µl of [$^3$H]-NAD$^+$ was added per well into a 96-well microtiterplate. The final concentrations in the incubation mixture were 2 µg/ml for the biotinylated histones, 2 mg/ml for the PVT-SPA beads, 2 µg/ml for the nicked DNA and between 5-10 µg/ml for the PARP-1 enzyme. After incubation of the mixture for 15 min. at room temperature, the reaction was terminated by adding 100 µl of 4 mM NAD$^+$ in incubation buffer (final concentration 2 mM) and plates were mixed.

The beads were allowed to sediment for at least 15 min. and plates transferred to a TopCountNXT™ (Packard) for scintillation counting, values were expressed as counts per minute (cpm). For each experiment, controls (containing PARP-1 enzyme and DMSO without compound), a blank incubation (containing DMSO but no PARP-1 enzyme or compound) and samples (containing PARP-1 enzyme and compound dissolved in DMSO) were run in parallel. All compounds tested were dissolved and eventually further diluted in DMSO. In first instance, compounds were tested at a concentration of $10^{-5}$ M. When the compounds showed activity at $10^{-5}$ M, a dose-response curve was made wherein the compounds were tested at concentrations between $10^{-5}$M and $10^{-8}$M. In each test, the blank value was subtracted from both the control and the sample values. The control sample represented maximal PARP-1 enzyme activity. For each sample, the amount of cpm was expressed as a percentage of the mean cpm value of the controls. When appropriate, —IC$_{50}$-values (concentration of the drug, needed to reduce the PARP-1 enzyme activity to 50% of the control) were computed using linear interpolation between the experimental points just above and below the 50% level. Herein the effects of test compounds are expressed as pIC$_{50}$ (the negative log value of the IC$_{50}$-value). As a reference compound, 4-amino-1,8-naphthalimide was included to validate the SPA assay. The tested compounds showed inhibitory activity at the initial test concentration of $10^{-5}$ M (see Tabel-2).

In vitro Filtration Assay for PARP-1 Inhibitory Activity

Compounds of the present invention were tested in an in vitro filtration assay assessing PARP-1 activity (triggered in the presence of nicked DNA) by means of its histone poly (ADP-ribosyl)ation activity using [$^{32}$P]-NAD as ADP-ribosyl donor. The radioactive ribosylated histones were precipitated by trichloroacetic acid (TCA) in 96-well filterplates and the incorporated [$^{32}$P] measured using a scintillation counter A mixture of histones (stock solution: 5 mg/ml in H$_2$O), NAD$^+$ (stock solution: 100 mM in H$_2$O), and [$^{32}$P]-NAD$^+$ in incubation buffer (50 mM Tris/HCl, pH 8; 0.2 mM DTT; 4 mM MgCl$_2$) was made. A mixture of the PARP-1 enzyme (5-10 µg/ml) and nicked DNA was also made. The nicked DNA was prepared as described in the in vitro SPA for PARP-1 inhibitory activity. Seventy-five µl of the PARP-1 enzyme/DNA mixture together with 1 µl of compound in DMSO and 25 µl of histones-NAD$^+$/[$^{32}$P]-NAD$^+$ mixture was added per well of a 96-well filterplate (0.45 µm, supplier Millipore). The final concentrations in the incubation mixture were 2 µg/ml for the histones, 0.1 mM for the NAD$^+$, 200 µM (0.5 µC) for the [$^{32}$P]-NAD$^+$ and 2 µg/ml for the nicked DNA. Plates were incubated for 15 min. at room temperature and the reaction was terminated by the addition of 10 µl ice cold 100% TCA followed by the addition of 10 µl ice-cold BSA solution (1% in H$_2$O). The protein fraction was allowed to precipitate for 10 min. at 4° C. and plates were vacuum filtered. The plates were subsequently washed with, for each well, 1 ml of 10% ice cold TCA, 1 ml of 5% ice cold TCA and 1 ml of 5% TCA at room temperature. Finally 100 µl of scintillation solution (Microscint 40, Packard) was added to each well and the plates were transferred to a TopCount-NXT™ (supplier: Packard) for scintillation counting and values were expressed as counts per minute (cpm). For each experiment, controls (containing PARP-1 enzyme and DMSO without compound), a blank incubation (containing DMSO but no PARP-1 enzyme or compound) and samples (containing PARP-1 enzyme and compound dissolved in DMSO) were run in parallel. All compounds tested were dissolved and eventually further diluted in DMSO. In first instance, compounds were tested at a concentration of $10^{-5}$M. When the compounds showed activity at $10^{-5}$M, a dose-response curve was made wherein the compounds were tested at concentrations between $10^{-5}$M and $10^{-8}$M. In each test, the blank value was subtracted from both the control and the sample values. The control sample represented maximal PARP-1 enzyme activity. For each sample, the amount of cpm was expressed as a percentage of the mean cpm value of the controls. When appropriate, IC$_{50}$-values (concentration of the drug, needed to reduce the PARP-1 enzyme activity to 50% of the control) were computed using linear interpolation between the experimental points just above and below the 50% level. Herein the effects of test compounds are expressed as $pIC_{50}$ (the negative log value of the $IC_{50}$-value). As a reference compound, 4-amino-1,8-naphthalimide was included to validate the filtration assay. The tested compounds showed inhibitory activity at the initial test concentration of $10^{-5}$M (see Tabel-2).

In Vitro Scintillation Proximity Assay (SPA) for TANK-2 Inhibitory Activity

Compounds of the present invention were tested in an in vitro assay based on SPA technology with Ni Flash plates (96 or 384 well).

In principle, the assay relies upon SPA technology for the detection of auto-poly (ADP-ribosyl)ation of TANK-2 protein using [$^3$H]-nicotinamide adenine dinucleotide ([$^3$H]-NAD$^+$) as ADP-ribosyl donor.

A stock solution of [$^3$H]-NAD$^+$/NAD was made by adding 64.6 μl of [$^3$H]-NAD$^+$ (0.1 mCi/ml, supplier: Perkin Elmer) and 46.7 μl NAD-stock (10.7 mM, stored at −20° C., supplier Roche) to 1888.7 μl assay buffer (60 mM Tris/HCl, pH 7.4; 0.9 mM DTT; 6 mM MgCl$_2$). The TANK-2 enzyme was produced as described in EP1238063. 60 μl of assay buffer, together with 1 μl of compound in DMSO, 20 μl of [$^3$H]-NAD$^+$/NAD and 20 μl of TANK-2 enzyme (final concentration 6 μg/ml) was added per well into a 96-well Ni-coated flash plate (Perkin Elmer). After incubation of the mixture for 120 min. at room temperature, the reaction was terminated by adding 60 μl of stopsolution (42.6 mg NAD in 6 ml H$_2$O). The plates were covered with a plate sealer and placed in a TopCountNXT™ (Packard) for scintillation counting. Values were expressed as counts per minute (cpm). For each experiment, controls (containing TANK-2 enzyme and DMSO without compound), a blank incubation (containing DMSO but no TANK-2 enzyme or compound) and samples (containing TANK-2 enzyme and compound dissolved in DMSO) were run in parallel. All compounds tested were dissolved and eventually further diluted in DMSO. In first instance, compounds were tested at a concentration of $10^{-5}$ M. When the compounds showed activity at $10^{-5}$ M, a dose-response curve was made wherein the compounds were tested at concentrations between $10^{-5}$M and $10^{-8}$M. In each test, the blank value was subtracted from both the control and the sample values. The control sample represented maximal TANK-2 enzyme activity. For each sample, the amount of cpm was expressed as a percentage of the mean cpm value of the controls. When appropriate, $IC_{50}$-values (concentration of the drug, needed to reduce the TANK-2 enzyme activity to 50% of the control) were computed using linear interpolation between the experimental points just above and below the 50% level. Herein the effects of test compounds are expressed as $pIC_{50}$ (the negative log value of the $IC_{50}$-value). As reference compounds, 3-aminobenzamide and 4-amino-1,8-naphthalimide were included to validate the SPA assay. Herein the assay was described using 96-well plates. In the assay using 384-well plates the same final concentrations were used and volumes were adapted. If 96-well plate results were available these results were incorporated in Table-2, otherwise the results from the 384-well plate assay were shown.

TABLE 2

| Co. No. | in vitro filter assay PARP-1 pIC50 | in vitro SPA assay PARP-1 pIC50 | in vitro SPA assay TANK-2 pIC50 |
|---|---|---|---|
| 1 | 6.333 | 6.691 | <5 |
| 2 | 5.804 | 6.59 | <5 |
| 3 | 5.988 | 6.867 | <5 |
| 4 | 5.642 | 6.257 | 5.158 |

TABLE 2-continued

| Co. No. | in vitro filter assay PARP-1 pIC50 | in vitro SPA assay PARP-1 pIC50 | in vitro SPA assay TANK-2 pIC50 |
|---|---|---|---|
| 5 | 5.759 | 6.458 | 5.121 |
| 6 | 5.877 | 6.778 | 5.86 |
| 7 | 5.49 | 6.535 | <5 |
| 8 | 5.792 | 6.848 | 5.247 |
| 9 | 5.661 | 6.445 | <5 |
| 10 | 5.745 | 6.658 | 5.143 |
| 11 | 5.566 | 6.655 | <5 |

The compounds can be further evaluated in a cellular chemo- and/or radiosensitization assay, an assay measuring inhibition of endogenous PARP-1 activity in cancer cell lines and eventually in an in vivo radiosensitization test.

The invention claimed is:

1. A compound of formula (I),

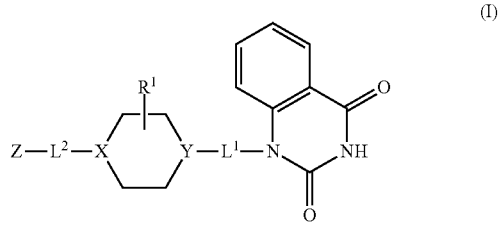

(I)

the N-oxide forms, the pharmaceutically acceptable addition salts and the stereo-chemically isomeric forms thereof, wherein each X is independently

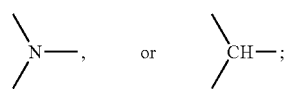

and when X is

then Y is

each Y is independently

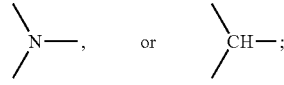

except when X is

then Y is

L¹ is a direct bond or a bivalent radical selected from —C$_{1-6}$alkanediyl-;

L² is a direct bond or a bivalent radical selected from carbonyl, —C$_{1-6}$alkanediyl-, -(hydroxy)C$_{1-6}$alkanediyl-, —C(O)—C$_{1-6}$alkanediyl- or —C$_{1-6}$alkanediyl-C(O)—;

R¹ is hydrogen or hydroxy; and

Z is hydrogen.

2. A compound as claimed in claim 1 wherein
each X is independently

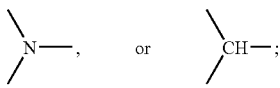

each Y is independently

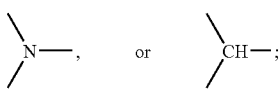

L¹ is a direct bond or a bivalent radical selected from —C$_{1-6}$alkanediyl-; L² is a direct bond or a bivalent radical selected from carbonyl, or —C$_{1-6}$alkanediyl-; R¹ is hydrogen or hydroxy.

3. A compound according to claim 1 wherein
each X is

each Y is

L¹ is a direct bond; L² is a direct bond; R¹ is hydrogen and Z is hydrogen.

4. A compound comprising:

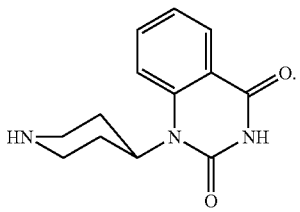

5. A pharmaceutical composition comprising pharmaceutically acceptable carriers and as an active ingredient a therapeutically effective amount of a compound as claimed in claim 1.

6. A process of preparing a pharmaceutical composition as claimed in claim 5 wherein the pharmaceutically acceptable carriers and the compound as claimed in claim 1 are intimately mixed.

7. A method of alleviating colon cancer, breast cancer, melanoma, glioblastoma, or lymphoma; protecting against cardiac dysfunction associated with doxorubicin; exhibiting a nephroprotective effect against ischemia-reperfusion injury; or protecting against peripheral neuropathy associated with cisplatin or taxol in a subject, said method comprising administering to the subject a therapeutically effective amount of a pharmaceutical composition comprising a pharmaceutically acceptable carrier and a compound of formula (I)

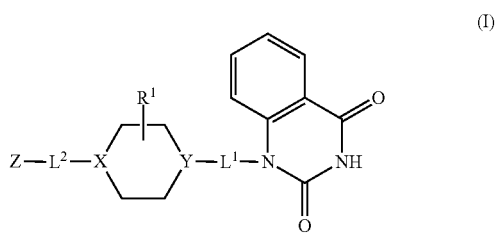

(I)

the N-oxide forms, the pharmaceutically acceptable addition salts and the stereo-chemically isomeric forms thereof, wherein
each X is independently

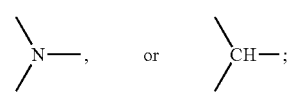

and when X is

then Y is

each Y is independently

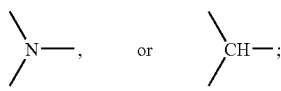

except when X is

then Y is

L$^1$ is a direct bond or a bivalent radical selected from —C$_{1-6}$alkanediyl-;
L$^2$ is a direct bond or a bivalent radical selected from carbonyl, —C$_{1-6}$alkanediyl-, -(hydroxy)C$_{1-6}$alkanediyl-, —C(O)—C$_{1-6}$alkanediyl- or —C$_{1-6}$alkanediyl-C(O)—;
R$^1$ is hydrogen or hydroxy;
Z is hydrogen.

8. The method of claim 7, further comprising chemosensitization.
9. The method of claim 7, further comprising radiosensitization.
10. A combination of a compound with a chemotherapeutic agent wherein said compound is a compound of formula (I)

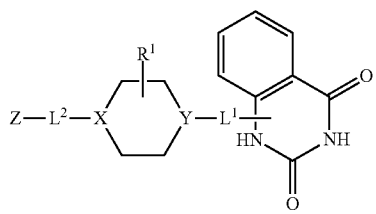

the N-oxide forms, the pharmaceutically acceptable addition salts and the stereo-chemically isomeric forms thereof, wherein
each X is independently

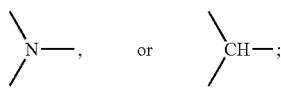

and when X is

then Y is

each Y is independently

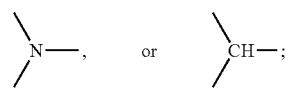

except when X is

then Y is

L$^1$ is a direct bond or a bivalent radical selected from —C$_{1-6}$alkanediyl-;
L$^2$ is a direct bond or a bivalent radical selected from carbonyl, —C$_{1-6}$alkanediyl-, -(hydroxyl)C$_{1-6}$alkanediyl-, —C(O)—C$_{1-6}$alkanediyl- or —C$_{1-6}$alkanediyl-C(O)—;
R$^1$ is hydrogen or hydroxyl;
Z is hydrogen.

11. A process for preparing a compound as claimed in claim 1, said process comprising:
a) reacting an intermediate of formula (II) with an intermediate of formula (III), wherein W is an appropriate leaving group, with the formation of a compound of formula (I-a), wherein X is

in a reaction-inert solvent and with the addition of an appropriate base, or

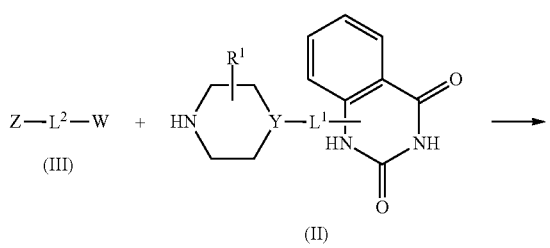

-continued

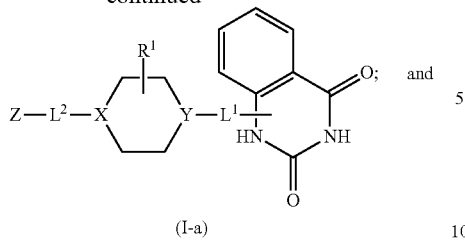

(I-a)

b) reacting an intermediate of formula (IV) with an intermediate of formula (V), wherein W is an appropriate leaving group, with the formation of a compound of formula (I-b), wherein Y is

in a reaction-inert solvent and with the addition of an appropriate base

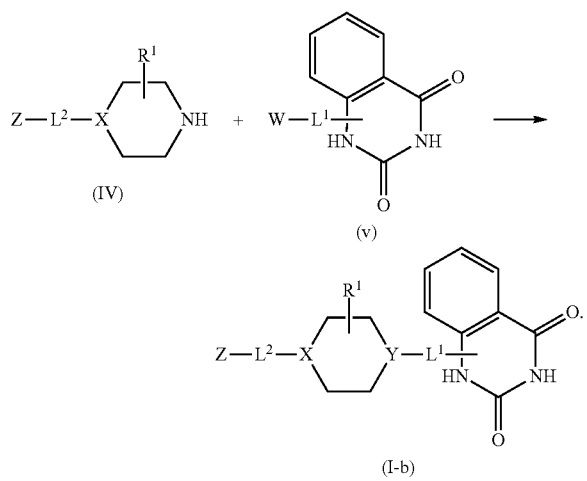

12. A compound according to claim 2 wherein each X is

each Y is

$L^1$ is a direct bond; $L^2$ is a direct bond; $R^1$ is hydrogen and Z is hydrogen.

13. A pharmaceutical composition comprising pharmaceutically acceptable carriers and as an active ingredient a therapeutically effective amount of a compound as claimed in claim 2.

14. A pharmaceutical composition comprising pharmaceutically acceptable carriers and as an active ingredient a therapeutically effective amount of a compound as claimed in claim 3.

15. A pharmaceutical composition comprising pharmaceutically acceptable carriers and as an active ingredient a therapeutically effective amount of a compound as claimed in claim 4.

16. A process of preparing a pharmaceutical composition as claimed in claim 13 wherein the pharmaceutically acceptable carriers and the compound as claimed in claim 2 are intimately mixed.

17. A process of preparing a pharmaceutical composition as claimed in claim 14 wherein the pharmaceutically acceptable carriers and the compound as claimed in claim 3 are intimately mixed.

18. A process of preparing a pharmaceutical composition as claimed in claim 15 wherein the pharmaceutically acceptable carriers and the compound as claimed in claim 4 are intimately mixed.

* * * * *